United States Patent
Iga et al.

(10) Patent No.: US 6,526,316 B2
(45) Date of Patent: Feb. 25, 2003

(54) IONTOPHORESIS METHOD

(75) Inventors: Katsumi Iga, Suita (JP); Yasuyuki Suzuki, Nishinomiya (JP); Masahiro Kawase, Inagawacho (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/207,605

(22) Filed: Dec. 9, 1998

(65) Prior Publication Data

US 2002/0007140 A1 Jan. 17, 2002

(30) Foreign Application Priority Data

Dec. 12, 1997 (JP) ............................. 9-343444

(51) Int. Cl.⁷ ............................. A61N 1/30
(52) U.S. Cl. ............................. 604/20
(58) Field of Search ............................. 604/20; 424/486, 424/449; 514/12

(56) References Cited

U.S. PATENT DOCUMENTS

| | | | |
|---|---|---|---|
| 5,607,915 A | * 3/1997 | Patton | 514/12 |
| 5,616,560 A | * 4/1997 | Geddes et al. | 514/12 |
| 5,747,453 A | * 5/1998 | Holladay et al. | 514/12 |
| 5,811,465 A | * 9/1998 | Huntington et al. | 514/772 |
| 5,857,992 A | * 1/1999 | Haak et al. | 604/20 |
| 5,861,438 A | * 1/1999 | MacLean et al. | 514/648 |
| 5,908,400 A | * 6/1999 | Higo et al. | 604/20 |
| 5,919,155 A | * 7/1999 | Lattin et al. | 604/20 |

FOREIGN PATENT DOCUMENTS

| | | |
|---|---|---|
| EP | 0 643 981 A1 | 3/1995 |
| EP | 0 747 092 A2 | 12/1996 |
| EP | 0 748 636 A2 | 12/1996 |
| EP | 0 813 879 A2 | 12/1997 |
| WO | 96/35447 | 11/1996 |
| WO | WO96/39423 | 12/1996 |

OTHER PUBLICATIONS

R. Lindsey et al., "Randomised controlled study of effect of parathyroid hormone on vertebral–bone mass and fracture incidence among postmenopausal women on oestrogen with osterporosis" The Lancet, vol. 350, No. 9077, pp. 550–555 (1997).

* cited by examiner

Primary Examiner—Michael J. Hayes
(74) Attorney, Agent, or Firm—Wenderoth, Lind & Ponack, L.L.P.

(57) ABSTRACT

A method for transdermal administration of parathyroid hormone by iontophoresis, which comprises applying electric current at least 2 times a day, which method is repeated one to four times each week, or an apparatus for the iontophoresis can be widely applied for not only the prevention or treatment of osteoporosis but also for general bone diseases which require promotion of bone morphogenesis, for example, treatment of ordinary fractures.

The method of the present invention produces excellent pharmacological effects such as few side effects and a high bioavailability in long term administration for the prevention and treatment of bone diseases.

16 Claims, 3 Drawing Sheets

IONTOPHORESIS METHOD

FIELD OF THE INVENTION

This invention relates to a method for transdermal administration of parathyroid hormone by iontophoresis, which comprises applying electric current with the mode of supply and non-supply intermittently, wherein the administration is repeated frequently every week.

PRIOR ART

Iontophoresis is a system for promoting transdermal administration with electricity. Its principle lies in promotion of transdermal administration of a drug molecule through a skin barrier based on forces with which a molecule usually positively charged with an electric current migrates from the anode to the skin in an electrolytic solution, while a negatively charged molecule migrates from the cathode to the skin (see Journal of Controlled Release, Vol. 18, 1992, p. 213–220; Advanced Drug Delivery Review, Vol. 9, 1992, p. 119 and Pharmaceutical Research, Vol. 3, 1986, p. 318–326).

Parathyroid hormone is clinically used as a diagnostic agent to test for the functioning of the parathyroid gland and is also being developed clinically as a promising drug for the treatment of osteoporosis. Drugs currently being used or developed clinically for the treatment of osteoporosis are classified into a group which suppresses bone resorption or into another group which promotes osteogenesis by increasing positively the bone mass.

Drugs for suppressing resorption of bone include calcitonin, bisphosphoric acid and estrogens. These drugs are applied to patients who are active in bone resorption to prevent or improve osteoporosis by reducing the amount of bone-loss through suppressing dissolution of calcium into blood. These drugs, however, do not have the effect of retrieving bone mass to its natural state, after the bone-loss. This is the most important goal in the treatment of osteoporosis. Therefore, these drugs are not expected to prevent fracture by increasing the bone mass in an osteoporotic patient whose bone mass has been greatly reduced.

On the other hand, drugs for promoting osteogenesis include vitamin K, fluorine preparations and hormones such as parathyroid hormone or bone morphogenetic protein (BMP) or growth hormones. Vitamin K and fluorine preparations have been clinically used but have not always produced excellent treatment results.

Parathyroid hormone has been known to promote bone resorption in addition to strongly promoting osteogenesis (D. W. Dempster et al, Endocrine Reviews, Vol. 14, 1993, p. 690). Therefore, in treating osteoporosis, it is important to utilize the hormone to produce only its osteogenic effect. For this purpose it may be significant to select a preferable mode of administration.

There are many reports, regarding the relationship between the administration mode and the effect of parathyroid hormone. It is recognized that intermittent injection is more effective for osteogenesis than administration methods where the hormone blood concentration is maintained for a long period of time (J. Reeve et al, J. Bone Miner. Res, Vol. 11, 1996, page 440). Therefore, from this point of view, clinical trials of the hormone have been conducted using repeated intermittent injections (R. Lindsay et al, Lancet, Vol. 350, 1997, p. 550).

Parathyroid hormone is a hormone secreted from the parathyroid glands. It is known that the hormone is secreted pulsatively at an interval of several tens minutes in a living body with normal functions. It also is known that in the living body, the blood hormone concentration is maintained as repetitions of pulsating blood concentrations which are far lower in peak values than what is obtained clinically by the usual injection of this hormone. Therefore, while avoiding side effects of the hormone, if the administration methods can make it possible to produce blood concentrations of parathyroid hormone as frequent pulses close to such natural secretion mode, it may be possible to increase bone mass. However, it is quite uncertain whether or not the bone resorption will interfere with the effect of the hormone produced by the administration method. In this connection, PCT International Patent Application Publication No. WO96/35447 discloses a way to increase the bone mass, if duration time in the blood of parathyroid hormone is set between 2 and 6 hours, preferably 4 hours in the above intermittent administration, as an administration mode for obtaining better therapeutic effects, as compared with a case of duration time of more than 6 hours (for example 8 hours) or a 1 hour or bolus administration of lesser duration time.

Generally, the treatment of osteoporosis needs administration of drugs over a long period of time, from several months to several years. From this point of view, a self-administration is preferable. With oral administration which is one possible self-administration method, parathyroid hormone is poorly absorbed through digestive mucous membranes, because it is poorly permeable through mucous membranes and is also degraded by enzymes in the digestive tract because it is a peptide. With other possible self-administration methods, there may be mentioned intranasal or transpulmonary administration. In order to attain desired absorption of a drug, these administration routes need addition of an enzyme inhibitor or a stimulative agent for promoting permeability through mucous membrane. Even using these administration methods, it is necessary to administer the hormone as many times as the number of desired pulses in order to produce blood pulsatile parathyroid hormone concentration. It is practically impossible to repeat such administrations at intervals of, for example, tens minutes or several hours during the long periods of treatment.

As another self-administration method, percutaneous administration is considered. Generally, absorption of a peptide in usual percutaneous administration is extremely low even with the use of an agent for promoting absorption or other additives, and, therefore, such an administration method would not be practical. Also, a usual percutaneous administration could not produce blood concentrations of multiple pulse type in a one time administration.

European Patent Application Publication No. 747092 discloses percutaneous administration of thyroid hormone by iontophoresis. This method makes it possible for parathyroid hormone to penetrate skin barrier (mainly stratum corneum) through which the hormone usually could not penetrate, depending on electric current. In the publication, it is described that the total of current application time is preferably not longer than 24 hours, more preferably about not longer than 12 hours and particularly not longer than 6 hours.

However, nothing has been known from the view point of side effects and pharmacological effects, as to the appropriate frequency of administration of electric current in long term administration of parathyroid hormone by iontophoresis.

SUMMARY OF THE INVENTION

This invention relates to a method for transdermal administration of parathyroid hormone by iontophoresis, which comprises applying electric current with the mode of supply and non-supply intermittently, wherein the administration is repeated frequently every week.

DETAILED DESCRIPTION OF THE INVENTION

The present inventors conceived controlling the electric current application modes (i.e. supply or non-supply of electric current) and administration frequency in transdermal administration of parathyroid hormone by iontophoresis. Based on this original conception, the present inventors made extensive studies and, as a result, found a method for transdermal administration of parathyroid hormone for preventing or treating bone diseases with less side effects and enhanced pharmacological effects, which comprises repeating a repeated pattern of administration at one to four times each week or at intervals of every other day, once every three days or once every four days. The present inventors made further extensive studies and completed the present invention.

This invention is directed to:
1. A method for transdermal administration of parathyroid hormone by iontophoresis, which comprises applying electric current at least 2 times a day, which method is repeated one to four times each week.
2. The method according to the item 1, wherein the electric current is applied from 2 to about 20 times in one day.
3. The method according to the item 1, wherein the electric current is applied from about 3 to about 5 times in one day.
4. The method according to the item 1, wherein the electric current is applied for about 10 minutes to about 6 hours per each application.
5. The method according to the item 1, wherein there is a rest interval of from about 20 minutes to about 6 hours between each successive application of electric current.
6. The method according to the item 1, wherein the electric current is applied for about 20 to 40 minutes, and there is a rest interval of about 20 to about 60 minutes between each successive application of electric current.
7. The method according to the item 1, wherein the electric current is applied for about 30 minutes, and there is a rest interval of about 45 minutes between each successive application of electric current.
8. The method according to the item 1, wherein there is at least a one day rest period between repetitions of the method.
9. The method according to the item 1, wherein the method is repeated each week on the same days.
10. The method according to the item 1, wherein the method is repeated once every week.
11. The method according to the item 1, wherein the method is repeated twice every week.
12. The method according to the item 1, wherein the method is repeated three times every week.
13. The method according to the item 1, wherein the method is repeated four times every week.
14. A method for transdermal administration of parathyroid hormone by iontophoresis, which comprises applying electric current at least 2 times a day, which method is repeated once or twice in a successive three day period.
15. A method for transdermal administration of parathyroid hormone by iontophoresis, which comprises applying electric current at least 2 times a day, which method is repeated every other day or once every three days.
16. A method for transdermal administration of parathyroid hormone by iontophoresis, which comprises applying electric current three to five times a day, one to three days each week, wherein the method is repeated weekly on the same days.
17. A method for transdermal administration of parathyroid hormone by iontophoresis, which comprises applying electric current at least 2 times a day, wherein there is at least a one day rest period between successive repetitions of the method.
18. A method for transdermal administration of parathyroid hormone by iontophoresis, which comprises repeating an administration cycle of supply and non-supply of electric current, which cycle is repeated from 2 to about 20 times per day.
19. A method for transdermal administration of parathyroid hormone by iontophoresis, which comprises repeating an administration cycle of supply and non-supply of electric current, which cycle is repeated from 2 to about 20 times per day, once or twice in a three day period.
20. A method for transdermal administration of parathyroid hormone by iontophoresis, which comprises repeating an administration cycle of supply and non-supply of electric current to repeatedly sharply increase and decrease the blood concentration of hormone, which cycle is repeated 2 to about 20 times per day.
21. A method for pulsatile transdermal administration of parathyroid hormone by iontophoresis, which comprises intermittently applying electric current to mimic the pattern of secretion of the hormone by the parathyroid gland.
22. The method according to the item 1, wherein the location of electric current application is varied every one to three applications.
23. The method according to the item 1, wherein the location of electric current application is the patient's arm.
24. The method according to the item 23 wherein the arm is forearm.
25. The method according to the item 23, wherein the arm is upperarm.
26. The method according to the item 23, wherein the arm is underarm.
27. The method according to the item 1, wherein the parathyroid hormone is hPTH(1-34).
28. An iontophoresis apparatus for use in the method for transdermal administration according to the item 1.
29. An iontophoresis apparatus for use in the method for transdermal administration according to the item 18.
30. The apparatus according to the item 28, used for preventing or treating bone diseases.

In the present iontophoresis administration, a drug is absorbed into blood in response to the electric current, therefore, the drug is delivered with supply of an electric current. The state of non-supply of electric current means a state where the drug absorption does substantially not occur.

In the present invention, the supply of electric current in one day is carried out at least 2 times in one day. It is preferable to carry out the supply of electric current in one day at from 2 to about 20 times, more preferably at from 2 to 10 times or from about 3 to 7 times, still more preferably from about 3 to 5 times.

A period of time for supply of electric current for one application is about 10 minutes to about 6 hours, preferably 10 minutes to 3 hours, more preferably about 10 nimutes to about 90 minutes or about 20 minutes to 60 minutes, still more preferably from about 20 minutes to 40 minutes, and especially preferably about 30 minutes.

The rest interval between each successive application of electric current is preferably from about 20 minutes to about 6 hours, from about 20 minutes to about 3 hours, more preferably from about 20 minutes to about 60 minutes, and especially preferably about 45 minutes.

It is preferable that (i) the electric current is applied for about 20 to about 40 minutes, and there is a rest interval of about 20 to about 60 minutes between each successive application of electric current, (ii) the electric current is applied for about 20 minutes, and there is a rest interval of about 30 to about 60 minutes, especially about 30 minutes, about 45 minutes or about 60 minutes between each successive application of electric current, (iii) the electric current is applied for about 30 minutes, and there is a rest interval of about 30 to about 60 minutes, especially about 30 minutes, about 45 minutes or about 60 minutes between each successive application of electric current, (iv) the electric current is applied for about 40 minutes, and there is a rest interval of about 30 to about 60 minutes, especially about 30 minutes, about 45 minutes or about 60 minutes between each successive application of electric current, (v) the electric current is applied for about 30 minutes, and there is a rest interval of about 45 minutes.

It is preferable that there is at least one day rest period between repetitions of the administration by iontophoresis.

It is preferable that the method is repeated each week on the same days.

It is preferable that the method is repeated once every week, twice every week, three times every week or four times every week.

It is preferable that the application by electric current at least 2 times a day is repeated once or twice in a successive three day period.

It is preferable that application by electric current is at least 2 times a day, which method is repeated every other day, or once every three days.

It is preferable that application by electric current is three to five times a day, one to three days each week, wherein the method is repeated weekly on the same days.

It is preferable that application by electric current is at least 2 times a day, wherein there is at least a one day rest period between successive repetitions of the method.

It is preferable to repeat an administration cycle of supply and non-supply of electric current, which cycle is repeated from 2 to about 20 times per day, once or twice in a three day period.

It is preferable to repeat an administration of supply and non-supply of electric current to repeatedly sharply increase and decrease the blood concentration of hormone, which administration is repeated 2 to about 20 times per day, in which the administration is carried out such that the concentration of PTH in the blood is rapidly increased and thereafter is rapidly decreased. For example, the administration is carried out in that the concentration of PTH in the blood is increased from 2 to 50 times of the normal value and decreased from ½ to ⅕ of the increased amount.

It is preferable that intermittent application of electric current mimics the pattern of secretion of the hormone by the parathyroid gland.

The locations of the electric current applications (i.e. the position to which a patch is put on) can be varied in every application (i.e. the administration by iontophoresis using a patch).

It is preferable that the location of electric current application is the patient's arm, such as forearm, upperarm or underarm etc., and further thigh, chest, abdomen and so on can be used.

The administration of the present method is carried out for a time until the reduced bone density is increased to the level that a bone fracture is prevented. For example, the administration of the present method is carried out from about 3 months to about 3 years, preferably about 6 months to one year and 6 months. In the administration, there may be a rest period, i.e. the administration is not carried our, for a period of about 3 months to one year.

As for the results, with iontophioresis, parathyroid hormone can penetrate skin to give a blood concentration of sharp pulse type. According to the present invention, it is possible to achieve a pulse type blood concentration of parathyroid hormone corresponding to the supply of electric current, and it is also possible to set non-supply of electric current for one to several times at a short time such as from about 1 second to 5 minutes during supply of electric current, as far as it does not reduce the blood concentration.

An apparatus for iontophoresis usable for transdermal administration is not limited to one particular model, and there may be used apparatuses for iontophoresis, for example, those disclosed in European Patent Application Publications No. 747092, No. 748636 or No. 813879. For example, as anode portion, there may be employed foil type silver electrode, agar gel which contains ion-exchange resin, a humectant (for example an amino acid such as L-proline, an amide compound such as urea, N-methyl-2-pyrrolidone, etc.) and an organic acid (for example citric acid, etc.), an anodal patch (area of a site which contacts skin is 5 to 20 $cm^2$) which comprises a sheet of hydrophilic membrane, the menbrane supporting the drug, for example, a membrane which is formed with a hydrophilized fluororesin such as Hydrophilic Durapore manufactured by Millipore Co., Ltd., or a coated type membrane made by non-woven polyester which is treated with cellulose acetate as wetting agents manufactured by Toyo Roshi Co. Ltd. As an example of cathode portion, there may be employed an apparatus for iontophoresis which comprises foil of silver chloride electrode and cathode patch of agar gel. It is preferable to constitute a program in the system to control the time of electric current.

There is no particular limitation for kinds of electric current in transdermal administration by iontophoresis, which may be exemplified by direct current or pulsating direct current which is disclosed in European Patent Aplication Publication No. 732121, preferably pulsating direct current. Frequency of pulsating direct current is suitably selected from a range of, preferably about 0.1 to 200 kHz, more preferably about 1 to 100 kHz, still more preferably about 5 to 80 kHz, especially 30 kHz, 40 kHz or 50 kHz. Ratio of supply to non-supply of pulsating direct current is suitably selected from a range of preferably about 1/100 to 20/1, more preferably about 1/50 to 15/1, most preferably about 1/30 to 10/1. A combination of frequency and ratio of supply to non-supply of electric current is particularly preferably 3/7 at 30 kHz, 4/6 at 40 kHz or 1/1 at 50 kHz.

In setting intensity of electric current (i.e. amperage), it is preferable to adopt a method for suitably adjusting electric voltage so that a constant current may be obtained, i.e. constant transport current. As preferable amperage, current may be employed which is as strong as possible within such a range that would not produce any damage to the skin, a range from about 0.01 mA/cm$^2$ to 0.5 mA/cm$^2$, more preferably 0.05 mA/cm$^2$ to 0.2 mA/cm$^2$, especially about 0.05 mA/cm$^2$, about 0.07 mA/cm$^2$ or about 0.1 mA/cm$^2$.

The applied voltage may be selected from wherein the range which will not injure the skin of a living body, and which does not adversely affect the transdermal absorption ratio, and is for example, about 1 to 30 V, preferably about 5 to 20 V, still more preferably about 5 to 10 V.

In the present iontophoresis method, the amount of the drug, which is transdermally absorbed, depends on the proportions of the concentration of the drug which is loaded on the membrane and the proportion of the intensity of electric current.

In the present specification, when abbreviations are used to show amino acids, peptides, etc., they are in accordance with those of IUPAC-IUB Commission on Biochemical Nomenclature or with conventional ones in this field. It should be also understood that where there is a possibility of existence of optical isomers with regard to amino acids, they are in the L-form unless specifically indicated.

Parathyroid hormone in the present invention is preferably human PTH [abbreviated as hPTH(1-84)] or its active fragment(1-34) at its N-terminus, etc. (G. W. Tregear et al, Endocrinology, vol. 93, 1973, p. 1349–1353), or its active fragment of hPTH(1-38) at its N-terminus and most preferably derivatives of hPTH(1-34) or hPTH(1-84). As those derivatives, there may be peptide of the formula (I): $R^{1"}$—Val—Ser—Glu—Leu—$R^{2"}$—His—Asn—$R^{3"}$—$R^{4"}$—$R^{5"}$—His—Leu—Asn—Ser—$R^{6"}$—$R^{7"}$—Arg—$R^{8"}$—Glu—$R^{9"}$—Leu—$R^{10"}$—$R^{11"}$—$R^{12"}$—Leu—Gln—Asp—Val—His—Asn—$R^{13"}$(I)[$R^{1"}$ means Ser or Aib, $R^{2"}$ means Met or a natural fat-soluble amino acid, $R^{3"}$ means Leu, Ser, Lys or an aromatic amino acid, $R^{4"}$ means Gly or D-amino acid, $R^{5"}$ means Lys or Leu, $R^{6"}$ means Met or a natural fat-soluble amino acid, $R^{7"}$ means Glu or a basic amino acid, $R^{8"}$ means Val or a basic amino acid, $R^{9"}$ means Trp or 2-(1,3-Dithiolan-2-yl)Trp, $R^{10"}$ means Arg or His, $R^{11"}$ means Lys or His, $R^{12"}$ means Lys, Gln or Leu, $R^{13"}$ means Phe or Phe-Nh$_2$] or their salts (see Japanese Patent Application Laid-open No. 32696/1993, No. 247034/1982, European Patent Application Publications No. 510662, No. 477885, No. 539491), etc.

An amount of parathyroid hormone per patch per one administration is about 10 μg/patch to 5000 μg/patch, preferably about 50 μg/patch to 1000 μg/patch, especially 200 μg/patch, 400 μg/patch or 800 μg/patch. In the present iontophoresis, normally, one patch is used per day.

The present iontophoresis administration of PTH is used for preventing or treating bone diseases such as osteoporosis in mammalian animals (e.g. human being, rat, dog, monkey, etc).

In order to accomplish more effective prevention or treatment of osteoporosis, in addition to parathyroid hormone, other drugs for osteoporosis may be used which are exemplified by Vitamin D, Vitamin K, Iburiflavon, calcitonins, bisphosphoric acids, estrogens, parathyroid-related peptides (PTHr) which show similar effect to parathyroid hormone, bone morphogenetic peptides (BMP) such as hPTHrP and its active fragments, BMP-2, BMP-4 or BMP-7, growth hormones or growth hormone-releasing peptide (GHrp).

Among the peptide hormones belonging to calcitonins, side effects upon their administration by injection may be reduced by transdermal administration using the administration mode of the present invention. Therefore, it is effective to administer such hormones together with parathyroid hormone by iontophoresis. As it takes generally a long period of time to prevent or treat osteoporosis, it is possible to administer these combination drugs at the same time the parathyroid hormone is administered, as well as before or after treatment by parathyroid hormone. Those administration times are judged depending on whether treatment is intended for established osteoporosis, or for osteopenia, which is so-called reserve osteoporosis.

A transdermal administration method or an apparatus for iontophoresis of the present invention can be widely applied for not only the prevention or treatment of osteoporosis but also for general bone diseases which require promotion of bone morphogenesis, for example, treatment of ordinary fractures. The present invention is further applicable for the treatment of a fragile tooth.

The method for transdermal administration by iontophoresis of the present invention is capable of producing efficiently frequent pulsatile blood parathyroid hormone levels, because application and non-application of electric current are repeated under specific conditions. The method of the present invention produces excellent pharmacological effects such as few side effects and a high bioavailability in long term administration for the prevention and treatment of bone diseases.

The effect of the present invention is larger than that of conventional administration methods such as once-a-week injection.

Furthermore, the effect of the present invention is larger than that of the conventional iontophoretic administration method where electric supply is limited to one time per administration and the blood-drug level does not show multiple pulses.

According to the present invention, the burden of the patient is decreased because of the easier self administration of the drug.

The present invention is superior to such conventional methods as above with respect to the improvement of the patient's compliance, and because of the saving of the number of the patch consumed the present invention is less expensive.

The present invention will be further explained in more detail by the following Reference Examples and Examples. The present invention should not be limited to these examples.

REFERENCE EXAMPLE 1

Figure 1:
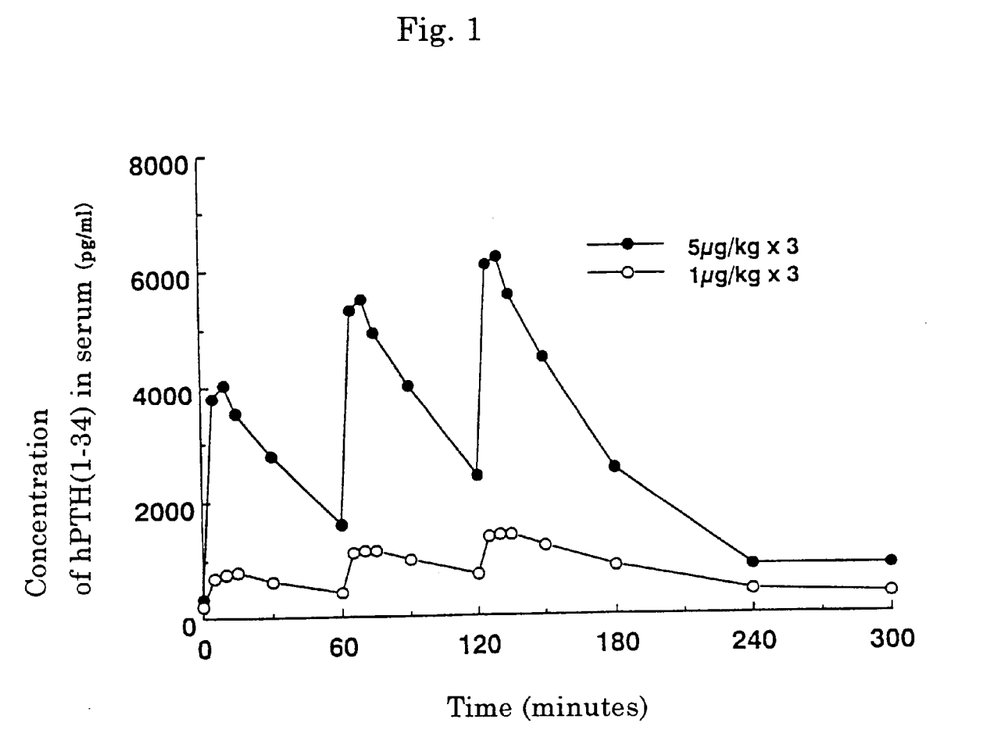
FIG. 1 shows the periodic concentration of hPTH(1-34) in serum of the Reference Example 1 mentioned below.

Female SD rats (12 weeks old) were ovariectomized and intradermally injected with an aqueous solution of hPTH(1-34) three times at 1 hour intervals at a one time administration dose of 1 μg/kg or 5 μg/kg. Concentration of hPTH (1-34) in serum of the rats was measured by radio immunoassay. Periodical concentrations of hPTH(1-34) in serum are shown in FIG. 1. The results shows blood concentration profiles of three sharp pulses and the maximum blood concentrations are proportional to the injected doses.

REFERENCE EXAMPLE 2

Female SD rats (12 weeks old) were ovariectomized and intradermally injected with an aqueous solution of hPTH(1-34) repeatedly using the following administration method and osteogenic effect was measured.

Subcutaneous injection of one time per day was repeated once/week (Wednesday), three times/week (Monday, Wednesday and Friday) or 7 times/week (everyday) for one month with the weekly administration dose of 35 μg/kg/ week. At 24 hours following the final administration, the rats were sacrificed, and bone mineral density of the distal third of the femur was measured by dual energy X-ray absorptionary (DXA). Pharmacological effects were evaluated by comparing with the results of two control groups, one being a sham group and the other being a group of ovariectomized rats to which a solution without hPTH(1-34) was administered. Bone mineral density after the administration is shown in Table 1. The results indicate that although bone amount was significantly decreased by the ovariectomization, PTH administration brought about a significant increase in the bone amount, and therefore, osteogenetic effect was increased in proportion to the administration frequency and the highest bone mineral density was obtained in the administration of 7 times/week.

TABLE 1

Comparison of bone mineral density:

| | Sham Group | Control Group | Ovariectomy Administration Frequency/week | | |
|---|---|---|---|---|---|
| | | | 1 | 3 | 7 |
| Bone mineral density (mg/cm$^2$) | 146†† | 134 | 136 | 144* | 154** |

Bone mineral density is an average of 6 samples.
††:p<0.01 vs. ovariectomy group (Student's t-test)
*:p<0.05, **:<0.01 vs. ovariectomy group (Dunnett's test)

REFERENCE EXAMPLE 3

Female SD rats (12 weeks old) were ovariectomized and injected subcutaneously with an aqueous solution of hPTH (1-34) repeatedly using the following administration methods.

Subcutaneous injection of three times per day at the interval of every one hour was repeated three times per week (Monday, Wednesday and Friday) for one month (total days of administration: 13 days) with the total administration dose of 35 μg/kg/week. At 24 hours following the final administration, the rats were sacrificed, and the bone mineral density of the distal third of the femur was measured by DXA. Pharmacological effects were evaluated by comparing results of three groups, the first being a sham group, the second being a group of ovariectomized rats to which a solution without hPTH(1-34) was administered and the third being a group to which the total dose of 35 μg/kg/week was administered one time/day in three times/week. Bone mineral density after the administration is shown in Table 2. The results indicate that although bone amount was significantly decreased by the ovariectomization, PTH administration brought about a significant increase in the bone amount, and therefore, in the two groups to which hPTH(1-34) was administered, a significant and high bone mineral density was obtained comparing with the ovariectomized control group and even in the case of administration of three times/week and effectiveness was hightened when administration frequency was increased by dividing the daily dose into three times and administering three times/day at the interval of 1 hour.

TABLE 2

Comparison of bone mineral density:

| | Sham Group | Control Group | Ovariectomy Administration Frequency/day | |
|---|---|---|---|---|
| | | | 1 | 3 |
| Bone mineral density (mg/cm$^2$) | 146†† | 134 | 144 | 153** |

Bone mineral density is an average of 6 samples.
††:p<0.01 vs. ovariectomy group (Student's t-test)
*:p<0.05, **:<0.01 vs. ovariectomy group (Dunnett's test)

REFERENCE EXAMPLE 4

Female SD rats (12 weeks old) were ovariectomized and injected subcutaneously with an aqueous solution of hPTH (1-34) repeatedly using the following administration methods.

Subcutaneous injection of three times per day at the interval of every one hour was repeated three times/week (Monday, Wednesday and Friday) for one month (total days of administration: 13 days) with the weekly administration doses of 7 μg/kg/week or 35 μg/kg/week. At 24 hours following the final administration, the rats were sacrificed, and bone mineral density of the distal third of the femur was measured by DXA. Pharmacological effects were evaluated by comparing with results of control groups, the first being a sham group, the second being a group of ovariectomized rats to which a solution without hPTH(1-34) was administered and the third being a group to which the dose was subcutaneously administered everyday (7 times/week) at once a day. Bone mineral density after the administration is shown in Table 3. The results indicate that although bone amount is significantly decreased by the ovariectomization, PTH administration brought about an increase of the bone amount significantly, and the group to which hPTH(1-34) was administered showed significantly high bone mineral density as compared with the control ovariectomized group. The results further indicated that a group to which hPTH (1-34) was administered three times/day at the interval of 1 hour by dividing the daily dose into three times brings about a high bone mineral density corresponding to a group to which hPTH(1-34) was administered everyday at one time/day.

TABLE 3

Comparison of bone mineral density:

| | Sham Group | Control Group | Ovariectomy Once/day(7 times/week) | | 3 times/day(9 times/week) | |
|---|---|---|---|---|---|---|
| | | | 7*** | 35*** | 7*** | 35*** |
| Bone mineral density (mg/cm$^2$) | 146†† | 134 | 141 | 155** | 137 | 153** |

Bone mineral density is an average of 6 samples.
††:p<0.01 vs. ovariectomy group (Student's t-test)
*:p<0.05, **:<0.01 vs. ovariectomy group (Dunnett's test)
***: (μg/kg/week)

REFERENCE EXAMPLE 5

Female SD rats (12 weeks old) were ovariectomized and subcutaneously injected with an aqueous solution of hPTH (1-34) 3 times in one day at the interval of 1 hour, the one administration being 10 μg/kg or 40 μg/kg, and the administration is repeated once every week (Wednesday) for 3 months.

Bone mineral density after the administration is shown in Table 4. The results indicate that although bone amount was significantly decreased by the ovariectomization, PTH administration brought about a significant increase of the bone amount, and that the group being administered once every week with hPTH(1-34) showed a higher bone mineral density than the ovariectomized control group, and this is a significant effect on the increased bone mineral density compared with the same level of the bone mineral density of the sham control group.

TABLE 4

Comparison of bone mineral density:

|  | Sham Group | Control Group | Ovariectomy | |
|---|---|---|---|---|
|  |  |  | 30 μg/kg/day administered group | 120 μg/kg/day administered group |
| Bone mineral density (mg/cm$^2$) | 159 ± 4** | 137 ± 1 | 152 ± 3** | 159 ± 3** |

Mean value ± SE (n = 7)
**p<0.01 (against the ovariectomized sham group)

EXAMPLE 1

Figure 2:
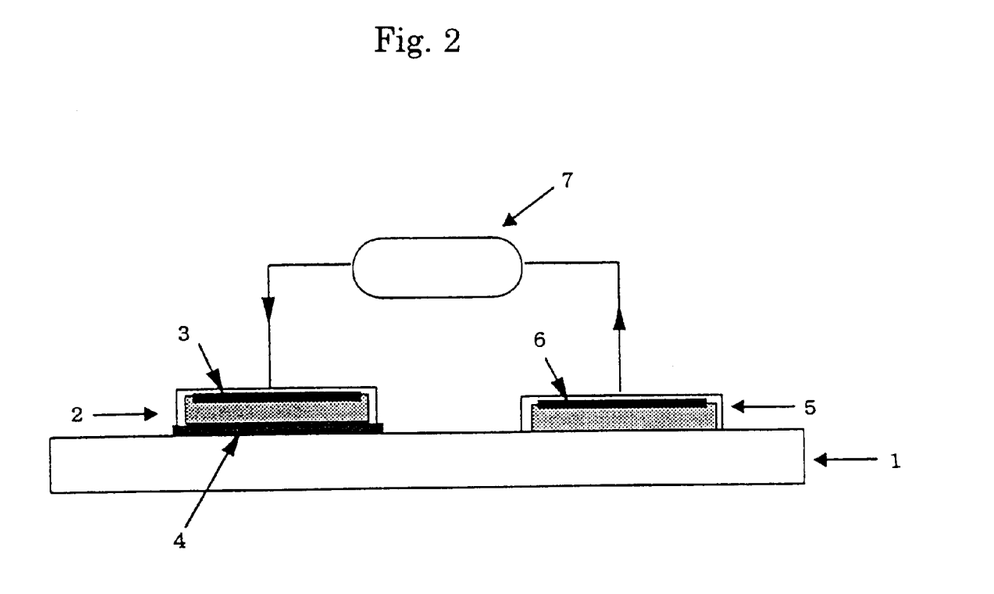
FIG. 2 shows an iontophoresis apparatus for transdermal administration by iontophoresis in the Example 1 mentioned below. In the drawing, 1 is skin, 2 is an anodal patch, 3 is silver electrode, 4 is a membrane supporting a drug, 5 is a cathodal patch, 6 is a silver chloride electrode and 7 is an electric generator.
Figure 3:
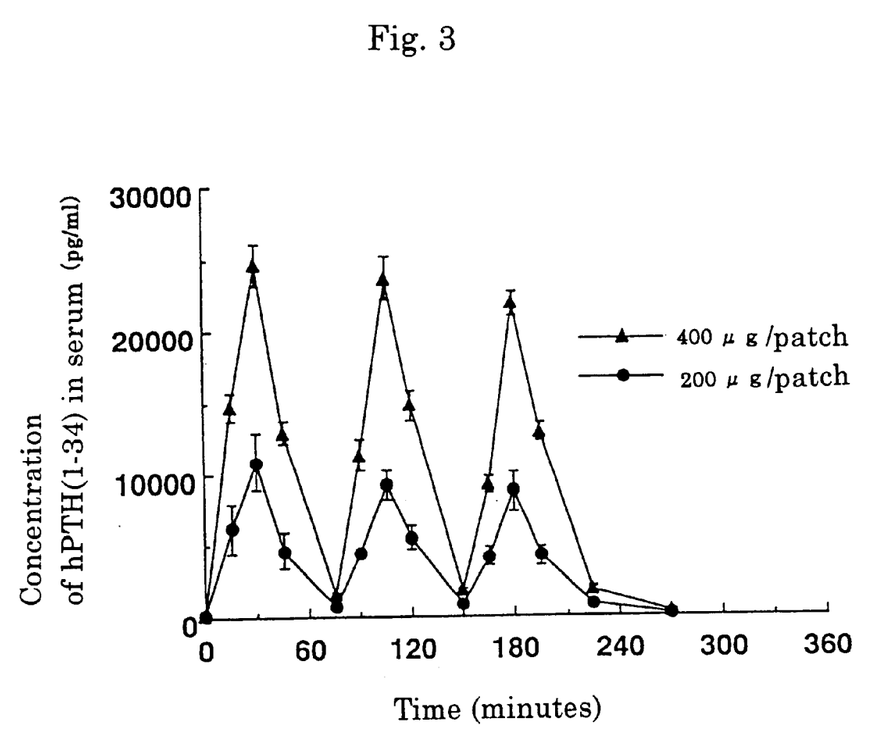
FIG. 3 shows the periodic concentration of hPTH(1-34) in serum in Example 1 mentioned below.

An apparatus for transdermal administration by iontophoresis was made, as shown in FIG. 2, which comprises an anode patch (area contacting skin is 9 cm$^2$) of a foil silver electrode, agar gel containing cholestyramine, which is an ion-exchange resign, and other additives, i.e. urea, L-proline, sodium benzoate, tri-sodium citrate dihydrates and thickener, whose components are shown in Table 5, and a thin film (hydrophilic Durapore membrane manufactured by Millipore Co.) supporting hPTH(1-34), and an cathode patch which comprises foil silver chloride electrode and agar gel. Hair on the abdominal skin of male, SD rats (7 weeks old) was shaved off. To the shaved part was attached the iontophoresis apparatus which comprises an anode patch containing 200 μg or 400 μg of hPTH(1-34) and a cathode patch without hPTH(1-34), as mentioned above. The apparatus was connected to an electric generator (50 kHz and 50% duty), and an electric current application using constant transport current (0.1 mA/cm$^2$) for 30 minutes and a 45-minute rest interval (corresponding to blood concentration of one pulse) was repeated three times. During the repetitions, blood was taken periodically, and concentration of hPTH(1-34) in serum was measured by radio immunoassay. Periodical changes in concentration of hPTH(1-34) in serum are shown in FIG. 3. The results show that there were pulsative blood concentrations with three sharp peaks.

TABLE 5

| Components of agar gel composition: | |
|---|---|
| Agar | 1.00% w/w |
| Xanthan gum | 0.25 |
| Locust bean gum | 0.25 |
| Cholestyramine hydrochloride resin | 5.00 |
| Urea | 5.00 |
| L-proline | 10.00 |
| Tri-sodium citrate dihydrate | 0.25 |
| Benzoic acid | 0.20 |
| Methyl p-hydroxy benzoate | 0.20 |
| Water | 77.85 |

EXAMPLE 2

Female, SD rats (6 months old) were ovariectomized and further bred for 3 months (body weight at the time: about 500 g.). Hair on the abdominal skin of the rats was shaved off. At the shaved site, transdermal administration of hPTH (1-34) was conducted repeatedly by the use of the iontophoresis apparatus and electric current as in Example 1, and osteogenic effect was measured. The doses were 0 μg/patch, 40 μg/patch, 120 μg/patch and 400 μg/patch. An administration was carried out by repeating three times a combination of current application for 30 minutes and a rest interval for 45 minutes (corresponding to a blood concentration of pulse pattern). Such administration methods were repeated three times/week, i.e. Monday, Wednesday and Friday, for one month (total days of administration: 13 days). At 24 hours following the final administration the rats were sacrificed, and bone mineral density of the distal third femur was measured by DXA. Pharmacological effects were evaluated by comparing results of two control groups, one being a sham group and the other being a group of the ovariectomized rats to which a solution without hPTH(1-34) was administered. Bone mineral density after the administration of the drug is shown in Table 6. The results indicate that the bone mineral density was increased depending on the dose.

TABLE 6

Comparison of bone mineral density:

|  | Sham Group | Control Group | Ovariectomy | | | |
|---|---|---|---|---|---|---|
|  |  |  | 3 times/week (μg/patch) | | | |
|  |  |  | 0 | 40 | 120 | 400 |
| Bone mineral density (mg/cm$^2$) | 155†† | 134 | 130 | 133 | 143** | 150** |

Bone mineral density is an average of 5 or 6 samples.
††:p<0.01 vs. overiectomy group (Student's t-test)
*:p<0.05, **:<0.01 vs. ovariectomy group (Dunnett's test)

EXAMPLE 3

Female SD rats (3 months old) which are ovariectomized and further bred for 1 week (body weight at the time: about 350 g.). Hair on the abdominal skin of the rats is shaved off. At the shaved site, transdermal administration of hPTH(1-34) is conducted repeatedly for 13 weeks on Monday and Wednesday by the use of the iontophoresis apparatus of Example 1 and electric current, according to the conditions mentioned below:
Administration amount of hPTH(1-34): 400 μg/patch, 800 μg/patch.
Current density: 0.1 mA/cm$^2$.
Application of electric current: At least 3 times a day, which comprises current application for 30 minutes and non-current application for 45 minutes.

EXAMPLE 4

Female SD rats (3 months old) which are ovariectomized and further bred for 1 week (body weight at the time: about 350 g.). Hair on the abdominal skin of the rats is shaved off. At the shaved site, transdermal administration of hPTH(1-34) are conducted repeatedly for 13 weeks on Wednesday by the use of the iontophoresis apparatus of Example 1 and electric current, according to the conditions mentioned below:
Administration amount of hPTH(1-34): 800 μg/patch.
Current density: 0.1 mA/cm$^2$.
Application of electric current: At least 3 or 4 times a day, which comprises current application for 30 minutes and non-current application for 45 minutes.

EXAMPLE 5

Female SD rats (3 months old) which are ovariectomized and further bred for 1 week (body weight at the time: about 350 g.). Hair on the abdominal skin of the rats is shaved off. At the shaved site, transdermal administration of hPTH(1-34) are conducted repeatedly for 13 weeks on Monday by the use of the iontophoresis apparatus of Example 1, wherein the agar gel is made by the composition shown in Table 7 mentioned below wherein N-methyl-2-pyrrolidine is used instead of urea (Table 5), and a Coated Type Membrane (Toyo Roshi Co., Ltd.) is used, and electric current as the conditions mentioned below:
Administration amount of hPTH(1-34): 800 μg/patch.
Current density: 0.1 mA/cm$^2$.
Application of electric current: At least 3 times a day, which comprises current application for 30 minutes and non-current application for 45 minutes.

TABLE 7

| Components of agar gel composition: | |
| --- | --- |
| Agar | 1.00% w/w |
| Xanthan gum | 0.25 |
| Locust bean gum | 0.25 |
| Cholestyramine hydrochloride resin | 5.00 |
| N-methyl-2-pyrrolidine | 5.00 |
| L-proline | 10.00 |
| Tri-sodium citrate dyhydrate | 0.25 |
| Citric acid | 0.25 |
| Benzoic acid | 0.20 |
| Methyl p-hydroxy benzoate | 0.20 |
| Water | 77.15 |

What we claim is:

1. A method for transdermal administration of parathyroid hormone by iontophoresis, which comprises applying a patch containing parathyroid hormone to a patient's skin, and applying an electric current to the patch to transdermally deliver parathyroid hormone into the patient's body, wherein the electric current is applied for about 20 to 40 minutes per application, wherein the electric current is applied from 2 to about 10 times in one day, wherein there is a rest interval of about 20 to about 60 minutes between each successive application of electric current, wherein the administration is repeated one to four times each week, and wherein the method administers a therapeutic amount of parathyroid hormone effective to treat or prevent bone disease.

2. The method according to claim 1, wherein the electric current is applied from about 3 to about 5 times in one day.

3. The method according to claim 1, wherein the electric current is applied for about 30 minutes, and there is a rest interval of about 45 minutes between each successive application of electric current.

4. The method according to claim 1, wherein there is at least a one day rest period between repetitions of the method.

5. The method according to claim 1, wherein the method is repeated each week on the same days.

6. The method according to claim 1, wherein the method is repeated once every week.

7. The method according to claim 1, wherein the method is repeated twice every week.

8. The method according to claim 1, wherein the method is repeated three times every week.

9. The method according to claim 1, wherein the method is repeated four times every week.

10. The method according to claim 1, wherein the location of electric current application is varied every one to three applications.

11. The method according to claim 1, wherein the location of electric current application is the patient's arm.

12. The method according to claim 11, wherein the arm is forearm.

13. The method according to claim 11, wherein the arm is upperarm.

14. The method according to claim 11, wherein the arm is underarm.

15. The method according to claim 1, wherein the parathyroid hormone is hPTH(1-34).

16. A method for preventing or treating a bone disease, comprising applying a patch containing parathyroid hormone to a patient's skin, and applying an electric current to the patch to transdermally and iontophoretically deliver parathyroid hormone into the patient's body, wherein the electric current is applied for about 20 to 40 minutes per application, wherein the electric current is applied from 2 to about 10 times in one day, wherein there is a rest interval of about 20 to about 60 minutes between each successive application of electric current, wherein the administration is repeated one to four times each week, and wherein the method administers a therapeutic amount of parathyroid hormone effective to treat or prevent bone disease.

* * * * *